US009980857B2

(12) United States Patent
Morimoto et al.

(10) Patent No.: US 9,980,857 B2
(45) Date of Patent: May 29, 2018

(54) ABSORBENT ARTICLE WITH LEG CUFFS

(71) Applicant: The Procter & Gamble Company, Cincinnati, OH (US)

(72) Inventors: Koichi Morimoto, Beijing (CN); Kazuaki Tameishi, Hyogo (JP)

(73) Assignee: The Procter & Gamble Company, Cincinnati, OH (US)

( * ) Notice: Subject to any disclaimer, the term of this patent is extended or adjusted under 35 U.S.C. 154(b) by 351 days.

(21) Appl. No.: 14/837,003

(22) Filed: Aug. 27, 2015

(65) Prior Publication Data

US 2016/0058625 A1    Mar. 3, 2016

(30) Foreign Application Priority Data

Aug. 27, 2014  (WO) .................... CN2014/085241
Feb. 4, 2015   (WO) .................... CN2015/0721915

(51) Int. Cl.
| | | |
|---|---|---|
| *A61F 13/15* | (2006.01) | |
| *A61F 13/20* | (2006.01) | |
| *A61F 13/494* | (2006.01) | |
| *A61F 13/49* | (2006.01) | |
| *A61F 13/496* | (2006.01) | |

(52) U.S. Cl.
CPC .......... *A61F 13/494* (2013.01); *A61F 13/49* (2013.01); *A61F 13/4902* (2013.01); *A61F 13/496* (2013.01); *A61F 13/49009* (2013.01); *A61F 13/4942* (2013.01); *A61F 2013/1556* (2013.01); *A61F 2013/15292* (2013.01); *A61F 2013/15422* (2013.01); *A61F 2013/15544* (2013.01); *A61F 2013/15552* (2013.01); *A61F 2013/49031* (2013.01); *A61F 2013/49041* (2013.01); *A61F 2013/4948* (2013.01); *A61F 2013/49093* (2013.01)

(58) Field of Classification Search
CPC ............ A61F 13/49009; A61F 13/4902; A61F 13/494; A61F 13/496; A61F 2013/49031; A61F 2013/49041; A61F 2013/49093; A61F 2013/4948
See application file for complete search history.

(56) References Cited

U.S. PATENT DOCUMENTS

| | | |
|---|---|---|
| 3,860,003 A | 1/1975 | Buell |
| 4,610,678 A | 9/1986 | Weisman |
| 4,673,402 A | 6/1987 | Weisman et al. |
| 4,834,735 A | 5/1989 | Alemany et al. |
| 4,888,231 A | 12/1989 | Angstadt |
| 4,892,536 A | 1/1990 | DesMarais et al. |
| 4,990,147 A | 2/1991 | Freeland |
| 5,037,416 A | 8/1991 | Allen et al. |
| 5,137,537 A | 8/1992 | Herron et al. |
| 5,147,345 A | 9/1992 | Young et al. |
| 5,151,092 A | 9/1992 | Buell et al. |

(Continued)

OTHER PUBLICATIONS

PCT International Search Report, dated Apr. 28, 2015 (5 pages).

*Primary Examiner* — Michele M Kidwell
(74) *Attorney, Agent, or Firm* — William E. Gallagher

(57) ABSTRACT

Disclosed is an absorbent article including a water permeable topsheet, a water impermeable backsheet, an absorbent core, an outer cover layer, and a pair of outer cuffs for providing leg gasketing function, wherein the pair of outer cuffs includes a cuff sealing disposed in a longitudinally extending manner, the cuff sealing located transversely between the absorbent core and the longitudinal side edge of the backsheet.

26 Claims, 7 Drawing Sheets

(56) References Cited

U.S. PATENT DOCUMENTS

| | | | |
|---|---|---|---|
| 5,260,345 | A | 11/1993 | Des Marais et al. |
| 5,269,775 | A | 12/1993 | Freeland et al. |
| 5,342,238 | A | 8/1994 | Segerpalm et al. |
| 5,387,207 | A | 2/1995 | Dyer et al. |
| 5,397,316 | A | 3/1995 | La Von et al. |
| 5,554,145 | A | 9/1996 | Roe et al. |
| 5,569,234 | A | 10/1996 | Buell et al. |
| 5,571,096 | A | 11/1996 | Dobrin et al. |
| 5,580,411 | A | 12/1996 | Nease et al. |
| 5,607,760 | A | 3/1997 | Roe |
| 5,609,587 | A | 3/1997 | Roe |
| 5,625,222 | A | 4/1997 | Yoneda et al. |
| 5,635,191 | A | 6/1997 | Roe et al. |
| 5,643,588 | A | 7/1997 | Roe et al. |
| 5,865,823 | A | 2/1999 | Curro |
| 6,004,306 | A | 12/1999 | Robles et al. |
| 6,107,537 | A | 8/2000 | Elder et al. |
| 7,626,073 | B2 | 12/2009 | Catalan |
| 2005/0215155 | A1 | 9/2005 | Young et al. |
| 2005/0234411 | A1 | 10/2005 | Ashton et al. |
| 2011/0196327 | A1 | 8/2011 | Chhabra et al. |

ABSORBENT ARTICLE WITH LEG CUFFS

FIELD OF INVENTION

This invention relates to absorbent articles such as diapers having leg cuffs with improved softness.

BACKGROUND OF THE INVENTION

It has long been known that absorbent articles such as diapers offer the benefit of receiving and containing urine and/or other bodily exudates. To effectively contain exudates, the article should provide a snug fit around the waist and legs of a wearer. Absorbent articles are known to have an absorbent main body comprising a topsheet, a backsheet, and an absorbent core.

Current diaper designs frequently include the use of an inner leg cuff to prevent leakage of bodily exudates and an outer leg cuff which provides a covering over the inner leg cuff to minimize the visibility of exudates through the inner leg cuff and provide a secondary means to capture bodily exudates should they breach the inner leg cuff. The inner leg cuff may be made using a hydrophobic nonwoven and may be disposed on the body-facing surface of the absorbent article or connected to the body-facing surface of the film backsheet layer. The inner leg cuff may be a substantially liquid impervious layer that prevents bodily exudates from passing out of the sides of the article and may also be highly breathable, allowing outside air to reach the skin to help maintain a healthy level of skin hydration. The outer leg cuff contains the outer leg elastic strands, which create the contraction forces and gathers, and can be sandwiched between the cuff material and backsheet material. In many current diapers, the outer leg cuff comprises the polymeric film layer of the backsheet to prevent molten adhesive from passing through the cuff to the garment-facing surface of the article during manufacturing, as well as to secure manufacturing tolerances when cutting, tracking, transferring, and combining materials. The polymeric film generally is used to prevent these issues, however, may result in a plastic like touch and may generate a paper like noise upon handling. Such sensory signals may connote a cheap or low quality diaper.

Based on the foregoing, there is a need for an absorbent article having leg cuffs that have improved tactile and perceived softness, while maintaining the performance of leakage protection. There is further a need for manufacturing such a wearable article in a reliable and economical manner.

SUMMARY OF THE INVENTION

The present invention relates to an absorbent article having a skin facing side, a garment facing side, a longitudinal axis, and a transverse axis, the absorbent article comprising:
1) a water permeable topsheet extending in the longitudinal direction and the transverse direction;
2) a water impermeable backsheet extending in the longitudinal direction and the transverse direction, and having a pair of longitudinal side edges;
3) an absorbent core disposed between the topsheet and the backsheet, the backsheet extending beyond the absorbent core in both the longitudinal direction and the transverse direction;
4) an outer cover layer disposed on the garment facing side of the backsheet, the outer cover layer at least coextensive with the backsheet; and
5) a pair of outer cuffs for providing leg gasketing function, each outer cuff comprising:
   a) a cuff sealing disposed in a longitudinally extending manner, the cuff sealing located transversely between the absorbent core and the longitudinal side edge of the backsheet,
   b) a first cuff elastic element comprising at least one elastic body disposed in a longitudinally extending manner, the first cuff elastic element located transversely inward of the longitudinal side edge of the backsheet, and no more transversely inward than 3 mm from the cuff sealing;
   c) a second cuff elastic element comprising at least one elastic body disposed in a longitudinally extending manner, the second cuff elastic element located transversely outward of the longitudinal side edge of the backsheet; wherein the tensile force of each elastic body of the second cuff elastic element is no more than 70% of the tensile force of any elastic body of the first cuff elastic element;
   d) a cuff gap located between the of the first cuff elastic element and the second cuff elastic element, the cuff gap having a transverse width of at least 3 mm; and
   e) a cuff fringe disposed in a longitudinally extending manner, the cuff fringe located transversely outward the second cuff elastic element, the cuff fringe having a transverse width of at least 5 mm;
   wherein the cuff sealing bonds all of the materials existing in the thickness direction of the article where the cuff sealing is located.

DEFINITIONS

Figure 1:
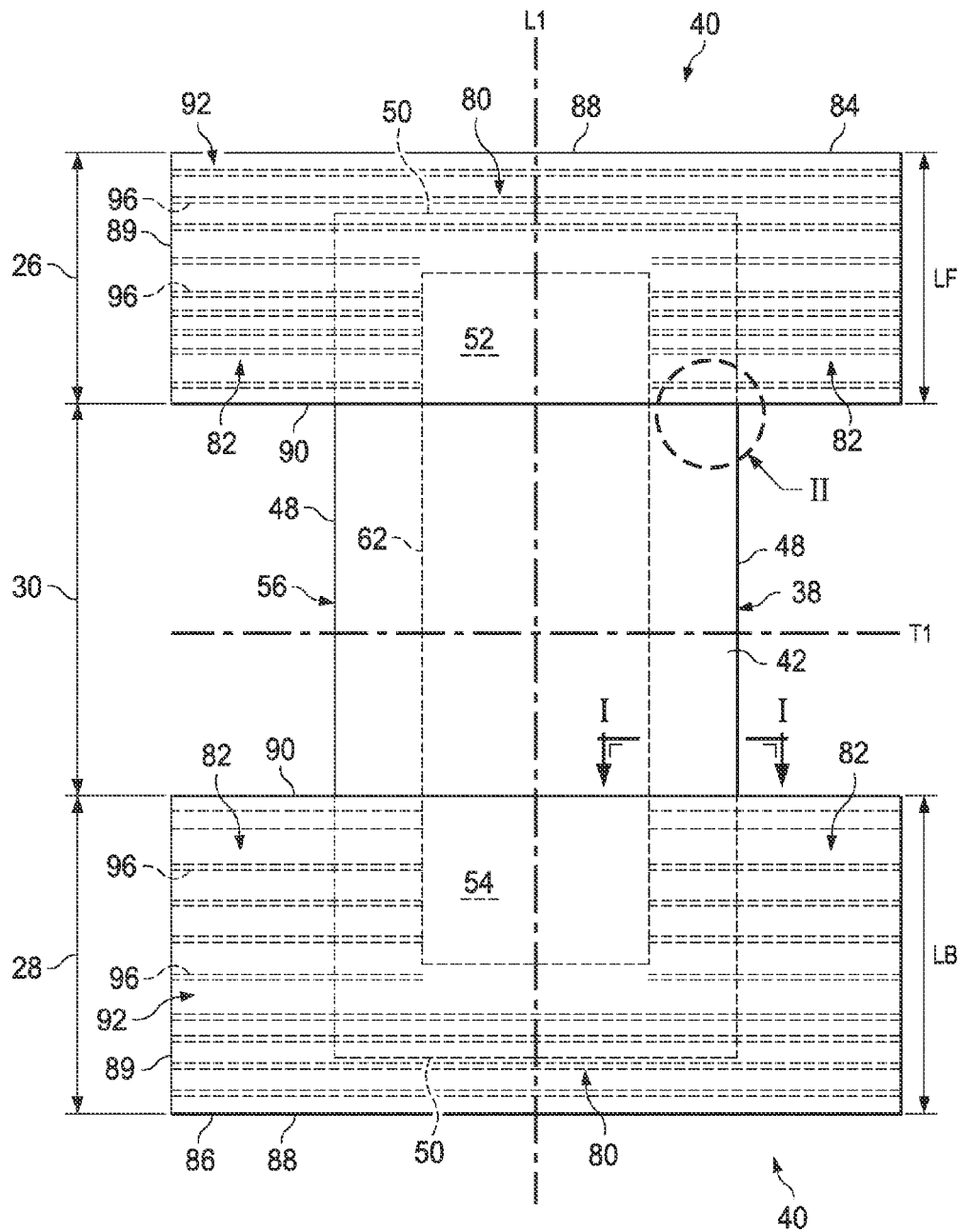
FIG. 1 is a schematic plan view of an exemplary absorbent article in a flat uncontracted condition showing the garment facing surface.

As used herein, the following terms shall have the meaning specified thereafter:

"Disposable," in reference to absorbent articles, means that the absorbent articles are generally not intended to be laundered or otherwise restored or reused as absorbent articles (i.e., they are intended to be discarded after a single use and, preferably, to be recycled, composted or otherwise discarded in an environmentally compatible manner).

"Absorbent article" refers to devices which absorb and contain body exudates and, more specifically, refers to devices which are placed against or in proximity to the body of the wearer to absorb and contain the various exudates discharged from the body. Exemplary absorbent articles include diapers, training pants, pull-on pant-type diapers (i.e., a diaper having a pre-formed waist opening and leg openings such as illustrated in U.S. Pat. No. 6,120,487), refastenable diapers or pant-type diapers, incontinence briefs and undergarments, diaper holders and liners, feminine hygiene garments such as panty liners, absorbent inserts, and the like.

"Pant" refers to disposable absorbent articles having a pre-formed waist and leg openings. A pant may be donned by inserting a wearer's legs into the leg openings and sliding the pant into position about the wearer's lower torso. Pants are also commonly referred to as "closed diapers", "prefastened diapers", "pull-on diapers", "training pants" and "diaper-pants."

"Longitudinal" refers to a direction running substantially perpendicular from a waist edge to an opposing waist edge of the article and generally parallel to the maximum linear dimension of the article.

"Transverse" refers to a direction perpendicular to the longitudinal direction.

"Inward" and "Outward" refer respectively to the location of an element relatively near to or far from the longitudinal or transverse centerline of a structure.

"Body-facing" and "garment-facing" refer respectively to the relative location of an element or a surface of an element or group of elements. "Body-facing" implies the element or surface is nearer to the wearer during wear than some other element or surface. "Garment-facing" implies the element or surface is more remote from the wearer during wear than some other element or surface (i.e., element or surface is proximate to the wearer's garments that may be worn over the disposable absorbent article).

"Disposed" refers to an element being located in a particular place or position.

"Joined" refers to configurations whereby an element is directly secured to another element by affixing the element directly to the other element and to configurations whereby an element is indirectly secured to another element by affixing the element to intermediate member(s) which in turn are affixed to the other element.

"Film" refers to a sheet-like material wherein the length and width of the material far exceed the thickness of the material. Typically, films have a thickness of about 0.5 mm or less.

"Water-permeable" and "water-impermeable" refer to the penetrability of materials in the context of the intended usage of disposable absorbent articles. Specifically, the term "water-permeable" refers to a layer or a layered structure having pores, openings, and/or interconnected void spaces that permit liquid water, urine, or synthetic urine to pass through its thickness in the absence of a forcing pressure. Conversely, the term "water-impermeable" refers to a layer or a layered structure through the thickness of which liquid water, urine, or synthetic urine cannot pass in the absence of a forcing pressure (aside from natural forces such as gravity). A layer or a layered structure that is water-impermeable according to this definition may be permeable to water vapor, i.e., may be "vapor-permeable."

"Extendibility" and "extensible" mean that the width or length of the component in a relaxed state can be extended or increased.

"Elasticated" and "elasticized" mean that a component comprises at least a portion made of elastic material.

"Elongatable material," "extensible material," or "stretchable material" are used interchangeably and refer to a material that, upon application of a biasing force, can stretch to an elongated length of at least about 110% of its relaxed, original length (i.e. can stretch to 10 percent more than its original length), without rupture or breakage, and upon release of the applied force, shows little recovery, less than about 20% of its elongation without complete rupture or breakage as measured by EDANA method 20.2-89. In the event such an elongatable material recovers at least 40% of its elongation upon release of the applied force, the elongatable material will be considered to be "elastic" or "elastomeric." For example, an elastic material that has an initial length of 100 mm can extend at least to 150 mm, and upon removal of the force retracts to a length of at least 130 mm (i.e., exhibiting a 40% recovery). In the event the material recovers less than 40% of its elongation upon release of the applied force, the elongatable material will be considered to be "substantially non-elastic" or "substantially non-elastomeric". For example, an elongatable material that has an initial length of 100 mm can extend at least to 150 mm, and upon removal of the force retracts to a length of at least 145 mm (i.e., exhibiting a 10% recovery).

"Elastomeric material" is a material exhibiting elastic properties. Elastomeric materials may include elastomeric films, scrims, nonwovens, and other sheet-like structures.

DETAILED DESCRIPTION OF THE INVENTION

FIG. 1 is a plan view of an exemplary, non-limiting embodiment of an absorbent article 20 of the present invention in a flat, uncontracted state (i.e., without elastic induced contraction). The garment-facing surface of the absorbent article 20 is facing the viewer. The wearable article 20 has a longitudinal centerline L1 which also serves as the longitudinal axis, and a transverse centerline T1 which also serves as the transverse axis. The wearable article 20 has a skin-facing surface, a garment-facing surface, a front region 26, a back region 28, and a crotch region 30. The front region 26 and the back region 28 may be seamed with seams 32 or joined by fastening means (not shown) to form two leg openings and a waist opening. The absorbent article 20 comprises a main body 38 to cover the crotch region of the wearer. In one embodiment, the absorbent article 20 may also comprise a front belt 84 and a back belt 86 (hereinafter may be referred to as "front and back belts"), the front and back belts 84, 86 forming a ring-like belt 40 (hereinafter may be referred to as "belt") extending transversely defining the waist opening. In such embodiment, the front and back belts 84, 86, and the main body 38 jointly define the leg openings. Alternatively, in another embodiment, the absorbent article may have the main body 38 extending to the waist opening and further comprising fastening means.

The outer periphery of the main body 38 is defined by longitudinal side edges 48 and transverse end edges 50. The main body 38 may have opposing longitudinal side edges 48 that are oriented generally parallel to the longitudinal centerline 100. However, for better fit, longitudinal side edges 48 may be curved or angled to produce, for example, an "hourglass" shape diaper when viewed in a plan view. The main body 38 may have opposing transverse end edges 50 that are oriented generally parallel to the transverse axis T1.

The main body 38 may comprise a water permeable topsheet 58 extending in the longitudinal direction and the transverse direction, a water impermeable backsheet 60 extending in the longitudinal direction and the transverse direction, and an absorbent core 62 disposed between the topsheet 58 and the backsheet 60. The backsheet may extend beyond the absorbent core in both the longitudinal direction and the transverse direction. The absorbent core 62 may have a body-facing surface and a garment facing-surface. The topsheet 58 may be joined to the absorbent core 62 and/or the backsheet 60. The backsheet 60 may be joined to the absorbent core 62 and/or the topsheet 58. It should be recognized that other structures, elements, or substrates may be positioned between the absorbent core 62 and the topsheet 58 and/or backsheet 60. While the topsheet 58, the backsheet 60, and the absorbent core 62 may be assembled in a variety of well-known configurations, preferred diaper configurations are described generally in U.S. Pat. Nos. 3,860,003; 5,151,092; 5,221,274; 5,554,145; 5,569,234; 5,580,411; and 6,004,306.

The topsheet 58 is generally a portion of the absorbent article 20 that may be positioned at least in partial contact or close proximity to a wearer. Suitable topsheets 58 may be manufactured from a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. The topsheet 58 is generally supple, soft feeling, and non-irritating to a wearer's skin. Generally, at least a portion of the topsheet 58 is water permeable, permitting bodily fluids to readily penetrate through the thickness of the topsheet 58. One topsheet 58 useful herein is available from BBA Fiberweb, Brentwood, Tenn. as supplier code 055SLPV09U.

Any portion of the topsheet 58 may be coated with a lotion or skin care composition as is known in the art. Examples of suitable lotions include those described in U.S. Pat. Nos. 5,607,760; 5,609,587; 5,635,191; and 5,643,588. The topsheet 58 may be fully or partially elasticized or may be foreshortened so as to provide a void space between the topsheet 58 and the absorbent core 62. Exemplary structures including elasticized or foreshortened topsheets are described in more detail in U.S. Pat. Nos. 4,892,536; 4,990, 147; 5,037,416; and 5,269,775.

The absorbent core 62 may comprise a wide variety of liquid-absorbent materials commonly used in disposable diapers and other absorbent articles. Examples of suitable absorbent materials include comminuted wood pulp, which is generally referred to as air felt creped cellulose wadding; melt blown polymers, including co-form; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In one embodiment, at least a portion of the absorbent core is substantially cellulose free and contains less than 10% by weight cellulosic fibers, less than 5% cellulosic fibers, less than 1% cellulosic fibers, no more than an immaterial amount of cellulosic fibers or no cellulosic fibers. It should be understood that an immaterial amount of cellulosic material does not materially affect at least one of the thinness, flexibility, and absorbency of the portion of the absorbent core that is substantially cellulose free. Among other benefits, it is believed that when at least a portion of the absorbent core is substantially cellulose free, this portion of the absorbent core is significantly thinner and more flexible than a similar absorbent core that includes more than 10% by weight of cellulosic fibers. The amount of absorbent material, such as absorbent particulate polymer material present in the absorbent core may vary, but in certain embodiments, is present in the absorbent core in an amount greater than about 80% by weight of the absorbent core, or greater than about 85% by weight of the absorbent core, or greater than about 90% by weight of the absorbent core, or greater than about 95% by weight of the core. Non-limiting examples of suitable absorbent cores 62 are described in greater details below.

Exemplary absorbent structures for use as the absorbent core 62 are described in U.S. Pat. Nos. 4,610,678; 4,673, 402; 4,834,735; 4,888,231; 5,137,537; 5,147,345; 5,342, 338; 5,260,345; 5,387,207; 5,397,316; and 5,625,222.

The backsheet 60 is positioned such that it extends beyond the absorbent core 62 on the garment-facing surface of the absorbent article 20 in both the longitudinal direction and the transverse direction. Backsheet 60 may be designed to prevent the exudates absorbed by and contained within the absorbent article 20 from soiling articles that may contact the absorbent article 20, such as bed sheets and undergarments. In certain embodiments, the backsheet 60 is substantially water-impermeable. Suitable backsheet 60 materials include films such as those manufactured by Tredegar Industries Inc. of Terre Haute, Ind. and sold under the trade names X15306, X10962, and X10964, and available from RKW Gronau GmbH, Gronau, Germany as supplier code PGBR4WPR. Other suitable backsheet 60 materials may include breathable materials that permit vapors to escape from the absorbent article 20 while still preventing exudates from passing through the backsheet 60. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends are available from Clopay Corporation, Cincinnati, Ohio under the name HYTREL blend P18-3097. Such breathable composite materials are described in greater detail in PCT Application No. WO 95/16746 and U.S. Pat. No. 5,865,823. Other breathable backsheets including nonwoven webs and apertured formed films are described in U.S. Pat. No. 5,571,096. An exemplary, suitable backsheet is disclosed in U.S. Pat. No. 6,107,537. Other suitable materials and/or manufacturing techniques may be used to provide a suitable backsheet including, but not limited to, surface treatments, particular film selections and processing, particular filament selections and processing, etc.

The outer cover layer 42 is located on the garment-facing side of the article 20. The outer cover layer 42 is at least coextensive with the backsheet 60. The outer cover layer 42 may be made of a soft, non-woven material. The outer cover layer 42 and the backsheet 60 may be joined together by adhesive or any other suitable material or method. A particularly suitable outer cover layer 42 is available from Corovin GmbH, Peine, Germany as supplier code A18AH0.

In one embodiment, the absorbent article 20 is a taped-type diaper further comprising fastening elements such as tapes, landing zone, and stretchable side panels 82.

In one embodiment, referring to FIG. 1, the absorbent article 20 is a pant-type diaper comprising a front belt 84, a back belt 86, and a main body 38, wherein the main body 38 comprises the topsheet 58; the backsheet 60; the absorbent core 62; the nonwoven outer cover layer 42; the cuff sealing 76; and the outer cuff 66. The pant-type article may have the center of the front belt 84 joined to a front waist panel 52 of the main body 38, the center of the back belt 86 joined to a back waist panel 54 of the main body 38, the front and back belt 84, 86 each having a left side panel 82 and a right side panel 82 where the main body 38 does not overlap, and the respective left and right side panels 82 of the front belt 84 and the back belt 86 are joined with each other only at the respective side edges to form a waist opening and two leg openings, each front belt 84 and back belt 86 having transversely continuous proximal and distal edges 90 88, the proximal edge 90 being located closer than the distal edge 88 relative to the longitudinal center of the article. The front and back belt 84, 86 may be formed by an inner sheet 94, an outer sheet 92, and a plurality of elastic bodies sandwiched therebetween and running in the transverse direction.

The vicinity of the longitudinal side edges 48 of the absorbent article 20 may be formed into a pair of outer cuffs 66 by at least the backsheet 60 and the outer cover layer 42, and also with the topsheet 58, and further with a cuff material 100 and elastic elements.

Figure 2:
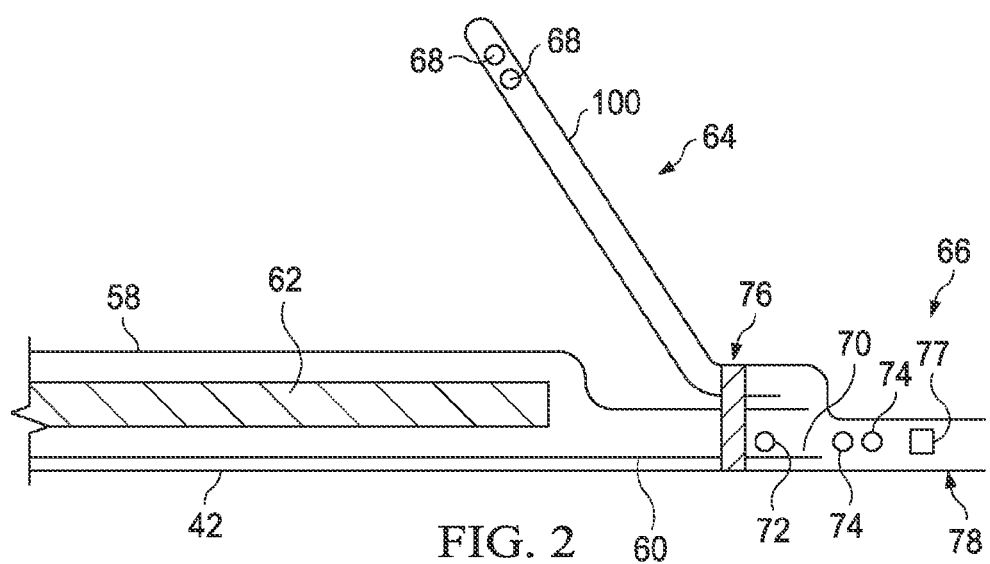
FIG. 2 is a schematic cross section view of an embodiment of the outer cuff of the present invention taken along line I-I of FIG. 1.
Figure 3:
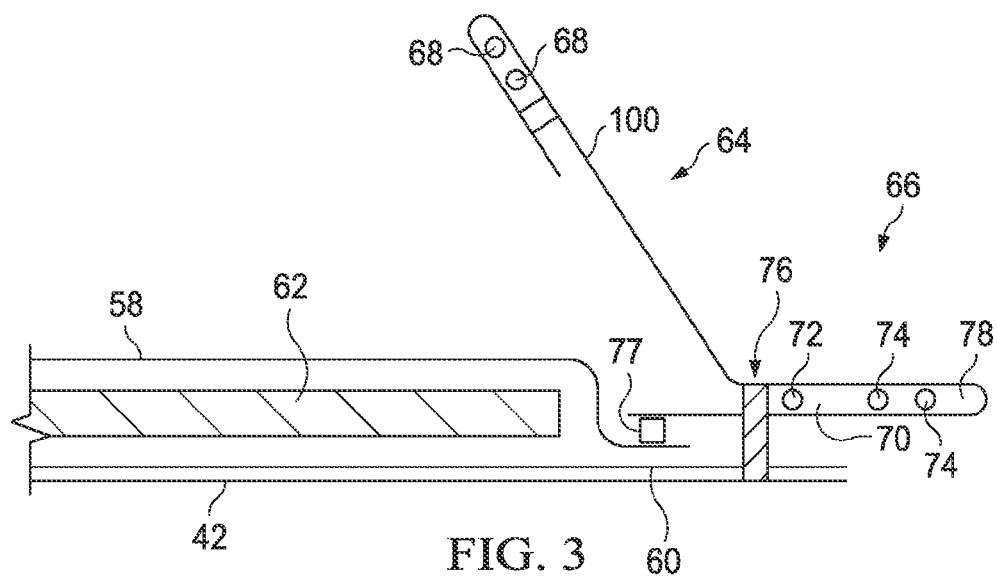
FIG. 3 is a schematic cross section view of another embodiment of the outer cuff of the present invention.
Figure 4:
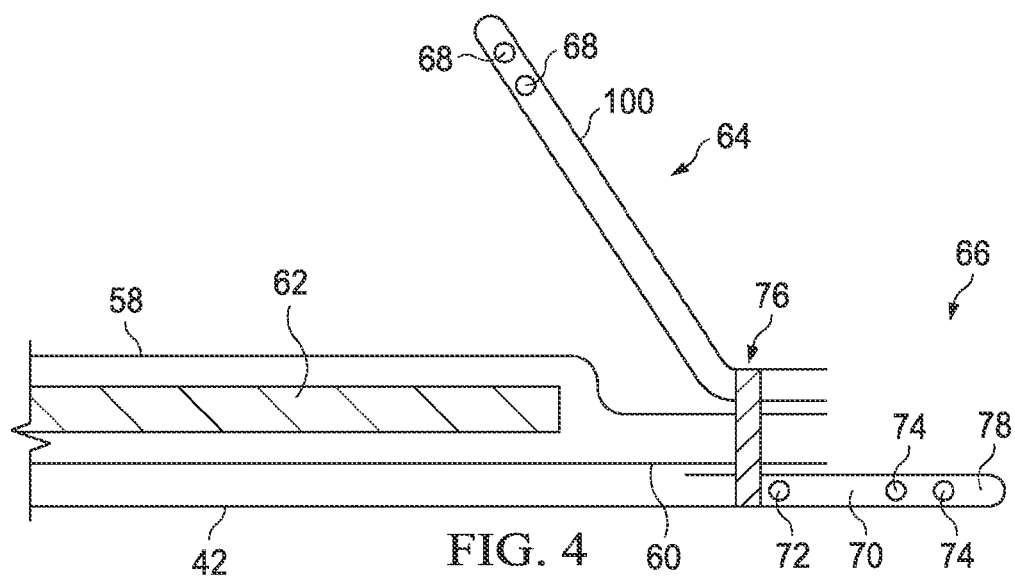
FIG. 4 is a schematic cross section view of another embodiment of the outer cuff of the present invention.

Referring to FIGS. 2-4, the outer cuff 66 of the present invention may comprise a pair of first cuff elastic elements 72 comprising at least one elastic body disposed in a longitudinally extending manner, each first cuff elastic element 72 located inward of each longitudinal side edge of the backsheet 60, for providing leg gasketing function. The first cuff elastic elements 72 are located in the vicinity of a pair of cuff sealings 76, and the first cuff elastic elements 72 and cuff sealing 76 cooperate to provide leakage protection along the longitudinal edges 48 of the main body 38. Each cuff sealing 76 is located transversely between the absorbent core 62 and each of the longitudinal side edges 48 of the backsheet 60. Each cuff sealing 76 bonds all of the materials existing in the thickness direction (hereinafter the "z-direction") of the article 20 where the cuff sealing 76 is located including, but not limited to, the backsheet 60 and any other material supporting the first cuff elastic element 72, and may span the entire longitudinal length of the topsheet 58. The first cuff elastic element 72 may be located no more inward, in the transverse direction, than 3 mm inward from the cuff sealing 76. The first cuff elastic element 72 may be located transversely inward or outward from the cuff sealing 76. The first cuff elastic element 72 may be bonded on the skin facing surface of the backsheet 60 as in FIG. 2, or located between cuff materials 100 as in FIG. 3, or located between the outer cover layers 42 as in FIG. 4. While FIGS. 2-4 all show the first cuff elastic element 72 located outward of the cuff sealing 76, the first cuff elastic element 72 may also be located within 3 mm inward of the cuff sealing 76. In whatever way the elastic elements are secured, the first cuff elastic element 72 may be located in a position wherein the backsheet 60 exists in the z-direction. By having the backsheet 60 support the first cuff elastic element 72 that may have higher tensile force than the other elastic bodies, this secures manufacturing tolerances of the main body 38 when cutting, tracking, transferring, and combining materials.

The absorbent article 20 of the present invention may further comprise a second cuff elastic element 74 comprising at least one elastic body disposed in a longitudinally extending manner, and located transversely outward of each longitudinal side edge 48 of the backsheet 60, and each elastic body providing a tensile force of no more than 70% of the tensile force of each elastic body of the first cuff elastic element 72. The second cuff elastic element 74 may function as an auxiliary, or aesthetic elastic means for leg gasketing.

By auxiliary function of the second cuff elastic element 74, what is meant is the function to assist the first cuff elastic element 72 to be placed and maintained in a position most suitable for providing leg gasketing and leakage protection. The auxiliary function of the second cuff elastic element 74 may include prevention of the first cuff elastic element 72 or the entire outer cuff 66 being tucked inwardly of the cuff sealing 76 when the article is worn.

When the first cuff elastic element 72 or the second cuff elastic element 74 are provided in a plurality of elastic bodies, the tensile force of each elastic body of the first cuff elastic element 72 and the second cuff elastic element 74 are compared. The first cuff elastic element 72 may comprise 1, or 2, or 3, elastic bodies. In one embodiment, the first cuff elastic element 72 may have an accumulative density of no more than 1500 dtex. The first cuff elastic element 72 may be prestretched at an elongation of no more than 330% elongation, when 0% elongation means its original length. The second cuff elastic element 74 may comprise 1 to 5, or 2 to 3, elastic bodies. In one embodiment, each elastic body of the second cuff elastic element 74 may have a density of no more than 680 dtex. The second cuff elastic element 74 may be prestretched to no more than 300% elongation. The second cuff elastic element 74 may be located in a position wherein the backsheet 60 does not exist in the z-direction. The second cuff elastic element 74 may be located between the cuff material 100 and the outer cover layer 42 as in FIG. 2, or located between cuff materials 100 as in FIG. 3, or located between the outer cover layers 42 as in FIG. 4.

The first and second cuff elastic elements 72, 74 may be spaced apart from each other by a cuff gap 70 having a transverse width of at least 3 mm, or at least 6 mm, or 6-16 mm, or 8-14 mm, or 8-12 mm. By providing such spacing between the first and second cuff elastic elements 72, 74, the location of the first cuff elastic element 72 relative to the backsheet 60 may be better controlled. In one embodiment, by providing such spacing between the first and second cuff elastic elements 72, 74, the main gasketing function of the first cuff elastic element 72 and the aesthetic function of the second cuff elastic element 74 may be better defined.

The absorbent article 20 of the present invention may further comprise a cuff fringe 78 extending longitudinally and located transversely outward the second cuff elastic element 74. The cuff fringe 78 may have a transverse width of at least 5 mm, or 5-8 mm, or 6-9 mm. The cuff fringe 78 may be formed by the cuff material 100 and outer cover layer 42 as in FIG. 2, or by layers of cuff materials 100 as in FIG. 3, or layers of the outer cover layer 42 as in FIG. 4. In one embodiment, the cuff fringe 78 is formed by only 2 layers of material. Such cuff fringe 78 may be soft and have good breathability. In one embodiment, the cuff fringe 78 is formed by one layer of the cuff layer 100 and one layer of the outer cover layer 42, as in FIG. 2. Such cuff fringe 78 may be economically made. In one embodiment, one of the cuff layer 100 or the outer cover layer 42 forming the cuff fringe 78 may be folded over itself to wrap the transverse edge of the cuff fringe 78, as in FIG. 3 or 4. Such cuff fringe 78 may connote softness at the edge, and provide good leakage protection.

In the present invention, the second cuff elastic element 74 and the cuff fringe 78 are devoid of the backsheet 60 material. In that this area of the outer cuff 66 is located most transversely outward of the absorbent article 20, it may be highly visible and frequently touched by the wearer or caregiver upon handling the absorbent article 20. As such, the visible, audio, and tactile signals provided by this area may be highly noticeable by one handling the absorbent article 20. By removing the backsheet 60 material from this area, the plastic like touch and appearance, as well as paper like noise that may otherwise be caused by the backsheet 60 material is significantly reduced. In one embodiment, by having the outer cover layer 42 form part of the cuff fringe 78, the softness of this area may be improved. Further, by having the majority of the outer cuff 66 free from the backsheet 60 or any other film material, the breathability of the outer cuff 66 may be improved. Overall, the outer cuff 76 of the present invention provides a pleasing tactile feel, good breathability, as well as perceived softness image, which may further connote high quality of the overall absorbent article 20.

Referring to FIGS. 2-4, the absorbent article 20 of the present invention may further comprise an inner cuff 64 extending transversely inward from the cuff sealing 76 or the vicinity thereof, the inner cuff 64 further providing leg gasketing function closer to the wearer. The inner cuff 64 may be formed by the cuff layer 100 and comprising an inner cuff 64 distal end projecting away from the cuff sealing 76. The distal end of the inner cuff 64 may be disposed with an inner cuff elastic element 68. The height of the inner cuff 64 from the cuff sealing 76 to the distal end may be at least about 30 mm, or at least about 32 mm, or at least about 35 mm.

Many variations are possible for forming the inner cuff 64 and the outer cuff 66.

In one embodiment, referring to FIG. 2, the cuff layer 100 forms a dual layer inner cuff 64 with the inner cuff elastic element 68 sandwiched therebetween, and the dual layers of cuff layer 100, the topsheet 58, the backsheet 60, and the outer cover layer 42 laid in this order from the skin facing side to the garment facing side, are bonded together by the cuff sealing 76. The outer cuff is mainly made from the cuff layer 100 and the outer cover layer 42 coextending transversely outward.

In one embodiment, referring to FIG. 3, the cuff layer 100 forms a single layer inner cuff 64 with the inner cuff elastic element 68 folded within cuff layer 100 which is then bonded to itself. The cuff layer 100 further forms the outer cuff sandwiching the first and second cuff elastic elements 72, 74, and folded under itself. In this embodiment, the two layers of the cuff layer 100, the backsheet 60, and the outer cover layer 42 laid in this order from the skin facing side to the garment facing side, are bonded together by the cuff sealing 76. The outer cuff 66 is mainly made from the cuff layer 100 extending transversely outward and folded under itself.

In one embodiment, referring to FIG. 4, the cuff layer 100 forms a dual layer inner cuff 64 with the inner cuff elastic element 68 sandwiched therebetween, while the outer cover layer 42 forms the outer cuff sandwiching the first and second cuff elastic elements 72, 74, and folding over itself. In this embodiment, the dual layers of cuff layer 100 for making the inner cuff 64, the topsheet 58, the backsheet 60, and the dual layers of outer cover layer 42 laid in this order from the skin facing side to the garment facing side, are bonded together by the cuff sealing 76. The outer cuff is mainly made from the outer cover layer 42 extending transversely outward and folded over itself.

The cuff sealing 76 is a bonding means which securely bonds multiple layers of material, such as by adhesive, by heat bond, by ultrasonic bond, or any combination thereof to provide leakage protection along the longitudinal edges 48 of the main body 38. The cuff sealing 76 may also be utilized for attaching material forming the inner cuff 64 to the main body 38. Besides the cuff sealing 76, other portions of the inner cuff 64 and outer cuff may be bonded with bonds 77 to prevent leakage, or to prevent elastic bodies from escaping the absorbent article 20.

In one embodiment, the cuff layer 100 is made from a substantially liquid impervious material. The material may be selected from the group consisting of an SMS nonwoven, SMMS nonwoven material, or a nonwoven component layer comprising "N-fibers".

Various nonwoven fabric webs may comprise spunbond, meltblown, spunbond ("SMS") webs comprising outer layers of spunbond thermoplastics (e.g., polyolefins) and an interior layer of meltblown thermoplastics. In one embodiment of the present invention, the cuff layer 100 comprises a nonwoven component layer having fine fibers ("N-fibers") with an average diameter of less than 1 micron (an "N-fiber layer") may be added to, or otherwise incorporated with, other nonwoven component layers to form a nonwoven web of material. In some embodiments, the N-fiber layer may be used to produce a SNS nonwoven web or SMNS nonwoven web, for example.

The N-fibers may be comprised of a polymer, e.g., selected from polyesters, including PET and PBT, polylactic acid (PLA), alkyds, polyolefins, including polypropylene (PP), polyethylene (PE), and polybutylene (PB), olefinic copolymers from ethylene and propylene, elastomeric polymers including thermoplastic polyurethanes (TPU) and styrenic block-copolymers (linear and radial di- and tri-block copolymers such as various types of Kraton), polystyrenes, polyamides, PHA (polyhydroxyalkanoates) and e.g. PHB (polyhydroxubutyrate), and starch-based compositions including thermoplastic starch, for example. The above polymers may be used as homopolymers, copolymers, e.g., copolymers of ethylene and propylene, blends, and alloys thereof. The N-fiber layer may be bonded to the other nonwoven component layers by any suitable bonding technique, such as the calender bond process, for example, also called thermal point bonding.

In some embodiments, the use of an N-fiber layer in a nonwoven web may provide a low surface tension barrier that is as high as other nonwoven webs that have been treated with a hydrophobic coating or a hydrophobic melt-additive, and still maintain a low basis weight (e.g., less than 15 gsm or, alternatively, less than 13 gsm). The use of the N-fiber layer may also provide a soft and breathable (i.e., air permeable) nonwoven material that, at least in some embodiments, may be used in single web layer configurations in applications which previously used double web layer configurations. Furthermore, in some embodiments, the use of the N-fiber layer may at least reduce the undesirable migration of hydrophilic surfactants toward the web and, therefore, may ultimately result in better leak protection for an associated absorbent article. Also, when compared to an SMS web having a similar basis weight, the use of a nonwoven web comprising the N-fiber layer may decrease the number of defects (i.e., holes or pinholes through the mechanical bond site) created during the mechanical bonding process. Nonlimiting examples of cuff layer materials particularly suitable herein include SMNS type web available from PGI Spain with tradename CoPHOB15 P11 V2, and SMS type available from Toray Polytech Nantong with tradename LIVSEN SMS 15. N-fibers are further discussed in WO 2005/095700 and U.S. patent application Ser. No. 13/024,844.

In one embodiment, the inner cuff 64 web of material has a hydrostatic head of greater than about 2 mbar, greater than about 3 mbar, greater than about 4 mbar. In one embodiment, the outer cuff 66 web of material has a hydrostatic head of less than about 200 mbar, less than about 100 mbar, less than about 75 mbar, less than about 50 mbar, less than about 25 mbar, less than about 15 mbar.

In one embodiment, the inner cuff 64 web of material has an opacity of from about 15% to about 50% hunter opacity; optionally from about 20% to about 45% hunter opacity. In one embodiment, the outer cuff 66 web of material has an opacity of from about 45% to about 75% hunter opacity; optionally from about 50% to about 70% hunter opacity; optionally less than about 75% hunter opacity; optionally less than about 70% hunter opacity.

In one embodiment, the inner cuff 64 web of material has an air permeability of less than about 50 m$^3$/m$^2$/min; optionally less than about 45 m$^3$/m$^2$/min. In one embodiment, the outer cuff 66 web of material has an air permeability of greater than about 5 m$^3$/m$^2$/min; optionally greater than about 10 m$^3$/m$^2$/min; optionally greater than about 15 m$^3$/m$^2$/min; optionally greater than about 20 m$^3$/m$^2$/min.

The inner cuff 64 may span the entire longitudinal length of the absorbent main body 38. The inner cuff 64 may be formed by the cuff material 100 and an elastic element 68 (such as elastic strands). The inner cuff 64 may further comprise a variety of substrates such as plastic films and woven or nonwoven webs of natural fibers (e.g., wood or cotton fibers), synthetic fibers (e.g., polyester or polypropylene fibers), or a combination of natural and synthetic fibers. In certain embodiments, the inner cuff 64 may comprise a nonwoven web such as spunbond webs, meltblown webs, carded webs, and combinations thereof (e.g., spunbond-meltblown composites and variants). Laminates may also be used. A particularly suitable inner cuff 64 may comprise a nonwoven available from BBA Fiberweb, Brentwood, Tenn. as supplier code 30926. A particularly suitable elastic member is available from Invista, Wichita, Kans. as supplier code T262P. Further description of diapers having inner barrier cuffs and suitable construction of such barrier cuffs may be found in U.S. Pat. Nos. 4,808,178 and 4,909,803. The inner cuff elastic element 68 may span the longitudinal length of the inner cuff 64. In other embodiments, the inner cuff elastic element 68 may span at least the longitudinal length of the inner cuff 64 within the crotch region 30. It is desirable that the inner cuff elastic element 68 exhibits sufficient elasticity such that the inner cuff 64 remains in contact with the wearer during normal wear, thereby enhancing the barrier properties of the inner cuff 64.

The inner cuff 64 and/or outer cuff 66 may be treated, in full or in part, with a lotion, as described above with regard to topsheets 58, or may be fully or partially coated with a hydrophobic surface coating as detailed in U.S. application Ser. No. 11/055,743, which was filed Feb. 10, 2005. Hydrophobic surface coatings usefully herein may include a non-aqueous, solventless, multicomponent silicone composition. The silicone composition includes at least one silicone polymer and is substantially free of aminosilicones. A particularly suitable hydrophobic surface coating is available from Dow Corning Mich., Salzburg as supplier code 0010024820.

Figure 5:
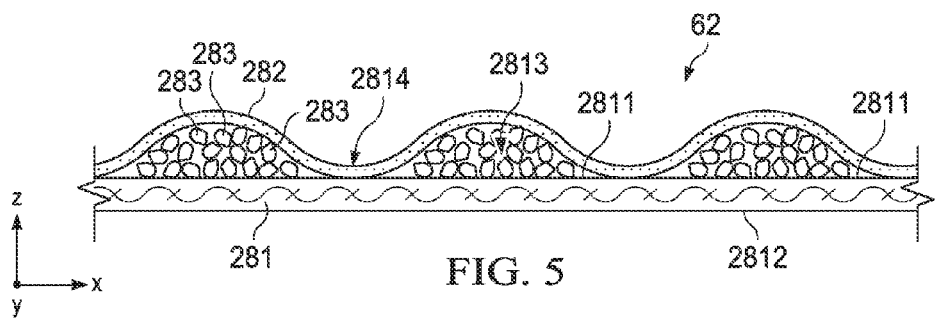
FIG. 5 is a schematic cross section view of an absorbent core suitable in one embodiment of the present invention.
Figure 6:
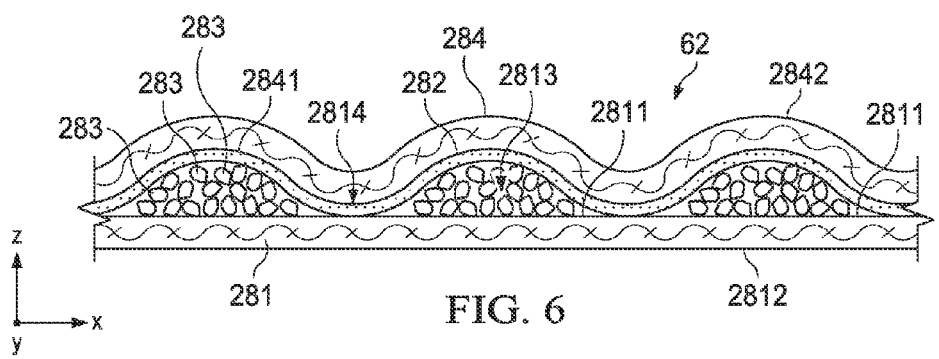
FIG. 6 is a schematic cross section view of another absorbent core suitable in one embodiment of the present invention.
Figure 7:
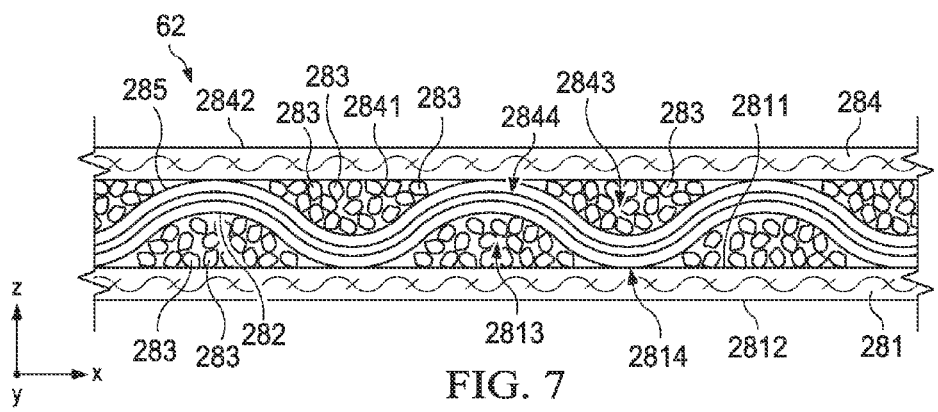
FIG. 7 is a schematic cross section view of another absorbent core suitable in one embodiment of the present invention.

In one embodiment, an absorbent article includes an absorbent core 62 that is substantially cellulose free. Cross-sectional views of examples of suitable absorbent cores 62 are schematically represented in FIGS. 5-7. The absorbent core 62 is the element of the absorbent article whose primary function is to absorb and retain liquid body exudates. Additional elements may be added between the topsheet 58 and the absorbent core 62 of an absorbent article to facilitate the acquisition and the distribution of body exudates. Such elements may include, for example, an acquisition layer and/or a distribution layer as it is well known in the art. The acquisition and/or distribution layers may themselves be substantially cellulose free (for example made entirely of a nonwoven material) or include a significant amount of cellulosic material. Although an absorbent core 62 generally includes absorbent materials in particulate form having a high retention capacity such as, for example absorbent polymers, these materials do not need to be present along the entire length of the absorbent core 62. It may be advantageous to provide an absorbent core 62 with a greater amount of absorbent material in the crotch region 30 and/or the front region 26 in comparison to the back region 28 which may include only a little amount, if any, of absorbent polymers. In one embodiment, an absorbent core 62 comprises first and second layers of material 281, 282 and an absorbent material 283 disposed between the first and second layers 281, 282. In one embodiment the first and second layers of material 281, 282 can be a fibrous material chosen from at least one of a nonwoven fibrous web, a woven fibrous web and a layer of thermoplastic adhesive material. Although the first and second layers 281, 282 can be made of a same material, in one embodiment, the first layer 281 is a nonwoven fibrous web and the second layer 282 is a layer of thermoplastic adhesive material. A nonwoven fibrous web 281 can include synthetic fibers, such as mono-constituent fibers of PE, PET and PP, multi-constituent fibers such as side by side, core/sheath or island in the sea type fibers. Such synthetic fibers may be formed via a spunbonding process or a meltblowing process. The nonwoven fibrous web 281 may include a single layer of fibers but it may also be advantageous to provide the nonwoven web with multiple layers of fibers such as multiple layers of spunbond fibers, multiple layers of meltblown fibers or combinations of individual layer(s) of spunbond and meltblow fibers. In one embodiment, the nonwoven web 281 can be treated with an agent (such as a surfactant) to increase the surface energy of the fibers of the web. Such an agent renders the nonwoven web more permeable to liquids such as urine. In another embodiment, the nonwoven web can be treated with an agent (such as a silicone) that lowers the surface energy of the fibers of the nonwoven web. Such an agent renders the nonwoven web less permeable to liquids such as urine.

The first layer 281 comprises a first surface 2811 and a second surface 2812 and at least regions 2813 of the first surface 2811 are in direct facial relationship with a significant amount of absorbent material 283. In one embodiment an absorbent material is deposited on the first surface 2811 in a pattern to form regions 2813 on the first layer 281, which are in direct facial relationship with a significant amount of absorbent polymer material 283 and regions 2814 on the first web that are in facial relationship with only an insignificant amount of absorbent material. By "direct facial relationship with a significant amount of absorbent material" it is meant that some absorbent material is deposited on top of the regions 2813 at a basis weight of at least 100 g/m$^2$, at least 250 g/m$^2$ or even at least 500 g/m$^2$. The pattern may include regions that all have the same shape and dimensions (i.e. projected surface area and/or height). In the alternative the pattern may include regions that have different shape or dimensions to form a gradient of regions. At least some of the regions 2813 can have a projected surface area of between 1 cm$^2$ and 150 cm$^2$ or even between 5 cm$^2$ and 100 cm$^2$. By "facial relationship with an insignificant amount of absorbent material" it is meant that some absorbent material may be deposited on top of the regions 2814 at a basis weight of less than 100 g/m$^2$, less than 50 g/m$^2$ or even substantially no absorbent material. At least some of the regions 2814 can have a projected surface area of between 1 cm² and 150 cm² or even between 5 cm² and 100 cm². The aggregate projected surface area of all the regions 2813 can represent between 10% and 90% or even between 25% and 75% of the total projected surface area of the first surface 2811 of the first layer 281. In one embodiment, the second layer 282 is a layer of a thermoplastic adhesive material. "Thermoplastic adhesive material" as used herein is understood to mean a polymer composition from which fibers are formed and applied to the absorbent material with the intent to immobilize the absorbent material in both the dry and wet state. Non-limiting examples of thermoplastic adhesive material may comprise a single thermoplastic polymer or a blend of thermoplastic polymers. The thermoplastic adhesive material may also be a hot melt adhesive comprising at least one thermoplastic polymer in combination with other thermoplastic diluents such as tackifying resins, plasticizers and additives such as antioxidants. In certain embodiments, the thermoplastic polymer has typically a molecular weight (Mw) of more than 10,000 and a glass transition temperature (Tg) usually below room temperature or −6° C. >Tg<16° C. In certain embodiments, typical concentrations of the polymer in a hot melt are in the range of about 20 to about 40% by weight. Exemplary polymers are (styrenic) block copolymers including A-B-A triblock structures, A-B diblock structures and (A-B)n radial block copolymer structures wherein the A blocks are non-elastomeric polymer blocks, typically comprising polystyrene, and the B blocks are unsaturated conjugated diene or (partly) hydrogenated versions of such. The B block is typically isoprene, butadiene, ethylene/butylene (hydrogenated butadiene), ethylene/propylene (hydrogenated isoprene), and mixtures thereof. Other suitable thermoplastic polymers that may be employed are metallocene polyolefins, which are polymers prepared using single-site or metallocene catalysts. In exemplary embodiments, the tackifying resin has typically a Mw below 5,000 and a Tg usually above room temperature, typical concentrations of the resin in a hot melt are in the range of about 30 to about 60% by weight, and the plasticizer has a low Mw of typically less than 1,000 and a Tg below room temperature, with a typical concentration of about 0 to about 15%.

The thermoplastic adhesive material 282 can be disposed substantially uniformly within the absorbent material 283. In the alternative, the thermoplastic adhesive material 282 can be provided as a fibrous layer disposed on top of the absorbent material 283 and the regions 2814 of the first surface 2811 that are in facial relationship with only an insignificant amount of absorbent material. In one embodiment, a thermoplastic adhesive material is applied at an amount of between 1 and 20 g/m², between 1 and 15 g/m² or even between 2 and 8 g/m². The discontinuous deposition of absorbent material on the first layer 281 imparts an essentially three-dimensional structure to the fibrous layer of thermoplastic material 282. In other words, the layer of thermoplastic adhesive material follows the topography resulting from the absorbent material 283 deposited on the first nonwoven fibrous web 281 and the regions 2814 that only include insignificant amounts of absorbent material. Without intending to be bound by any theory, it is believed that the thermoplastic adhesive materials disclosed herein enhance immobilization of the absorbent material in a dry and wet state.

In one embodiment, the absorbent core 62 may further comprise a second layer of a nonwoven fibrous material 284. This second layer 284 may be provided of the same material as the nonwoven fibrous layer 281, or in the alternative may be provided from a different material. It may be advantageous for the first and second nonwoven fibrous layers 281, 284 to be different in order to provide these layers with different functionalities. In one embodiment, the surface energy of the first nonwoven layer 281 can be different than the surface energy of the second nonwoven layer 284. In one embodiment, the surface energy of the second nonwoven layer 284 is greater than the surface energy of the first nonwoven layer 281. Among over benefits, it is believed that when the surface energy of the second nonwoven layer 284 is greater than the surface energy of the first nonwoven layer 281, liquids such as urine will be able to penetrate the second nonwoven layer 284 more easily in order to reach and be retained by the absorbent material while at the same time reducing the chances that the liquid may penetrate and go through the first layer 281. This may be particularly advantageous when the first nonwoven layer 281 is disposed against the backsheet of an absorbent article. The different surface energies of each layer may be obtained, for example, by applying a different amount of an agent such as a surfactant to the second nonwoven layer 284 than the amount of surfactant (if any) applied to the first nonwoven layer 281. This may also be achieved by applying a different type of surfactant to the second nonwoven layer 284 than the surfactant applied to the first nonwoven layer 281. This may still be achieved by applying a material to the first nonwoven layer 281 that lowers its surface energy. In addition to having different surface energies, or in the alternative, the first and second nonwoven fibrous layers 281, 284 may also be different structurally. In one embodiment, the first nonwoven layer 281 may include different layers of fibers than the second nonwoven layer 284. For example, the second nonwoven layer 284 may only include one or more layers of spunbond fibers whereas the first nonwoven layer 281 includes one or more layers of spunbond fibers and one or more layers of meltblown fibers. In another embodiment, both nonwoven fibrous layers 281, 284 may include one or more layers of spunbond fibers and one or more layers of meltblown fibers but the first and second layers 281, 284 differ in terms of at least one of the chemical composition of the fibers used to form the nonwoven material, the denier of the fibers and/or the basis weight of the nonwoven material. In addition to or in the alternative than the above the first and second nonwoven layers 281, 284 may also differ in terms of at least one of their respective hydrohead values, their respective porosity, their respective Frazier permeability and their respective tensile properties. The second nonwoven layer 284 may applied directly on top of the first nonwoven layer 281, the absorbent material 283 and the thermoplastic adhesive material 282. As a result, the first and second nonwoven layers 281 and 284 further encapsulate and immobilize the absorbent material 283.

The regions 2813 may have any suitable shape in the x-y dimension of the absorbent core 62. In one embodiment, the regions 2813 form a pattern of disc that are spread on the first surface 2811 of the first web 281. In one embodiment, the regions 2813 form a pattern of longitudinal "strips" that extend continuously along the longitudinal axis of the absorbent core 62 (i.e. along the y dimension). In an alternative embodiment, these strips may be are arranged to form an angle of at between 10 and 90 degrees, between 20 and 80 degrees, between 30 and 60 degrees, or even 45 degrees relative to the longitudinal axis of the absorbent article.

In one embodiment, the second nonwoven layer 284 has a first surface 2841 and a second surface 2842 and an absorbent material 283 applied to its first surface 2841 in order to form a pattern of regions 2843 that are in direct facial relationship with a significant amount of absorbent material 283 and regions 2844 on the first surface 2841 that are in facial relationship with only an insignificant amount of absorbent material as previously discussed. In one embodiment, a thermoplastic adhesive material 285 may further be applied on top of the second nonwoven layer 284 as previously discussed in the context of the first web/absorbent material/thermoplastic adhesive material composite. The second nonwoven layer 284 may then be applied on top of the first nonwoven layer 281. In one embodiment, the pattern of absorbent material present on the second nonwoven layer 284 may be the same as the pattern of absorbent material present on the first nonwoven layer 281. In an other embodiment, the patterns of absorbent material that are present on the first and second nonwoven layers 281, 284 are different in terms of at least one of the shape of the regions, the projected surface areas of the regions, the amount of absorbent material present on the regions and the type of absorbent material present on the regions. It is believed that when the patterns of absorbent material that are present on the first and second nonwoven layers 281, 284 are different, each layer/absorbent composite may have different functionalities such as for example, different absorbent capacities and/or different acquisition rates of liquids. It can be beneficial for example to provide an absorbent core 62 with a structure where the second pattern formed by the regions 2843 of absorbent material (i.e. on the second nonwoven layer 284) exhibits a slower acquisition rate than the first pattern of regions 2813 of absorbent material in order to allow liquids, such as urine, to reach and be absorbed by the absorbent material deposited on the first nonwoven layer 281 before expansion of the absorbent material in the regions 2843. Such a structure avoids any significant gel blocking by the absorbent material present in the regions 2843. It can also be advantageous to apply the second layer 284/absorbent material/thermoplastic adhesive material composite in such a way that at least some of or even all of the regions 2813 of the first nonwoven layer 281 that are in direct facial relationship with a significant amount of absorbent material are also in substantial facial relationship with corresponding regions 2844 of the second web 284, which are in facial relationship with an insignificant amount of absorbent material.

The absorbent core 62 may also comprise an auxiliary adhesive which is not illustrated in the figures. The auxiliary adhesive may be deposited on at least one of or even both the first and second nonwoven layers 281, 284 before application of the absorbent material 283 in order to enhance adhesion of the absorbent material as well as adhesion of the thermoplastic adhesive material 282, 285 to the respective nonwoven layers 281, 284. The auxiliary adhesive may also aid in immobilizing the absorbent material and may comprise the same thermoplastic adhesive material as described hereinabove or may also comprise other adhesives including but not limited to sprayable hot melt adhesives, such as H.B. Fuller Co. (St. Paul, Minn.) Product No. HL-1620-B. The auxiliary adhesive may be applied to the nonwoven layers 281, 284 by any suitable means, but according to certain embodiments, may be applied in about 0.5 to about 1 mm wide slots spaced about 0.5 to about 2 mm apart. Non-limiting examples of suitable absorbent material 283 include absorbent polymer material such as cross linked polymeric materials that can absorb at least 5 times their weight of an aqueous 0.9% saline solution as measured using the Centrifuge Retention Capacity test (Edana 441.2-01).

Figure 8:
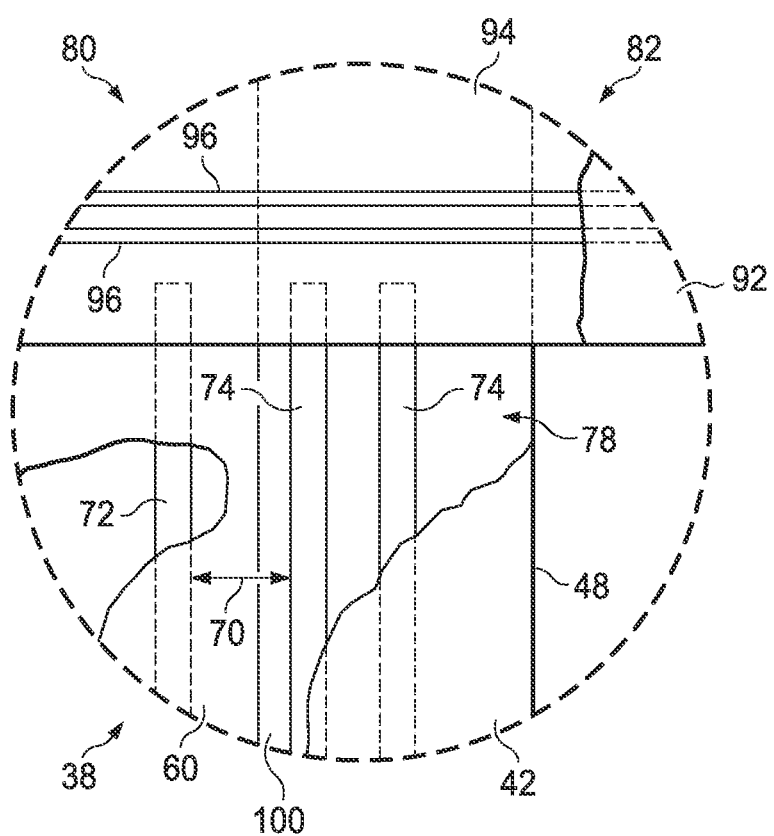
FIG. 8 is an exploded plan view of an embodiment of the outer cuff of the present invention taken along area II of FIG. 1.

Referring back to FIG. 1 and as described above, in one embodiment, the absorbent article 20 is a pant-type diaper comprising a front belt 84, a back belt 86, and a main body 38, the front and back belt 84, 86 formed by an inner sheet 94, an outer sheet 92, and a plurality of elastic bodies 96 sandwiched therebetween and running in the transverse direction. Referring to FIG. 8 which is an exploded view of area II of FIG. 1, the relationship between the elastic bodies 96 of the elastic belt 40 and the first and second cuff elastic elements 72, 74 of the outer cuff 66 are described. In the vicinity of the proximal edge 90 of either the front or back belt 84, 86, the elastic bodies 96 of the elastic belt 40 and the first and second cuff elastic elements 72, 74 of the outer cuff 66 may be disposed very close to each other, separated only by a number of sheets, for example, separated only by the inner sheet 94, the outer cover layer 42, and the backsheet 60. When the tensile force of the belt elastic bodies 96 are transmittable to the tensile force of the first and second cuff elastic elements 72, 74, this may lead to a number of disadvantages. For one, this may make the leg opening less flexible. In another, this may interfere with the softness of this area. In yet another, this may make transferring of the assembled article less efficient, by having points of elastic bodies crossing in more or less perpendicular directions.

Accordingly, in one embodiment, the front belt 84, the back belt 86, and the main body 38 of the present invention may be so configured such that the tensile force of any of the first and second cuff elastic elements 72, 74 are not transmitted to any elastic body 96 of the front or back belts 84, 86. To prevent the transmitting of the tensile force, in one embodiment, the main body 38 may be unattached, or not joined, to the front and back belts 84, 86 in the area where the first and second cuff elastic elements 72, 74 overlap in the thickness direction of the article. In another embodiment to prevent the transmitting of the tensile force, the belt elastics 96 may be located longitudinally outward of the first and second cuff elastic elements 72, 74, as in FIG. 8.

The absorbent article of the present invention may be made by processes well known for making a tape-type absorbent article or a pant-type absorbent article including, but not limited to, forming a continuous web of a main body 208, forming a continuous web of other elements of the article such as front and back belts 184, 186, and assembling such elements. For forming pant-type absorbent articles such as in FIG. 1 in high speed, the continuous web of the main body 208 may be suitably made by advancing the web in the longitudinal direction of the article, while the continuous webs of the front and back belts 184, 186 may be suitably made by advancing the webs in the transverse direction of the article. Hence, a transferring of elements may be required during the process of assembling the article.

Figure 9:
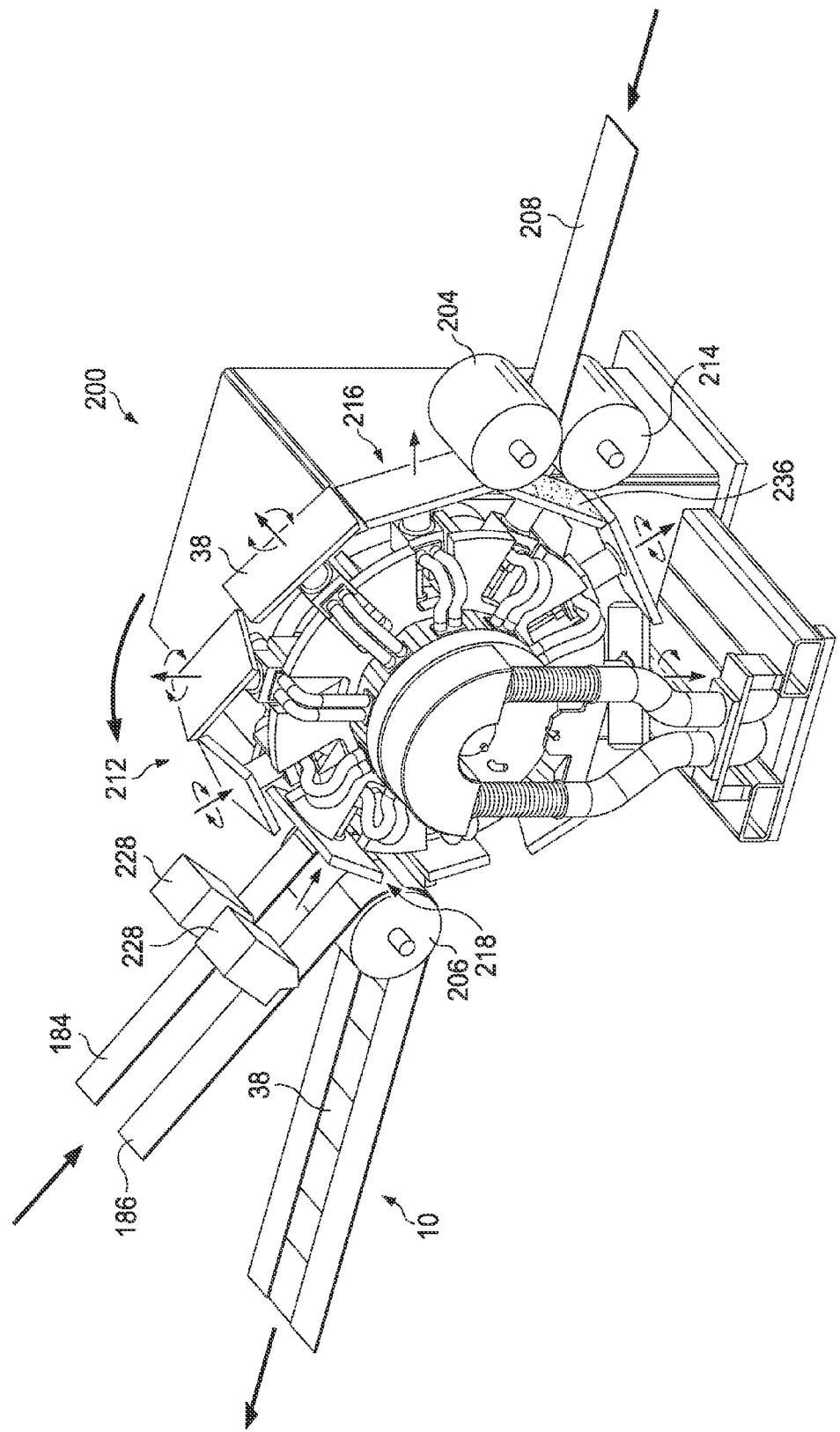
FIG. 9 is a schematic view of a suitable process for making an embodiment of the present invention.

As shown in FIG. 9, for assembling the article of the present invention, a continuous web 208 for making the main body 38 may be advanced by being fed on a roll or other conveying mechanism toward the first moving carrier member 204. The direction in which the continuous web 208 is advanced is considered the machine direction. Once a portion of the web 208 long enough to form a main body 38 is engaged with the first moving carrier member 204 and/or is engaged with a portion of a transfer member 212 of the transfer assembly 200, a knife integral to the first moving carrier member 204 may cut the web 208 into discrete main bodies 38 against an anvil roll 214. The knife may be a flex knife, a die cutter, a shear knife, or any other suitable knife or cutting device or mechanism. Knife and anvil roll 214 technology is generally known in the art. In other embodiments, previously cut main bodies 38 may be fed on the conveyor toward the first moving carrier member 204.

Each transfer member 212 may comprise a transfer surface 236 on an end of the transfer member 212 most distal from the rotation axis. The transfer surface 236 may be configured to pick up one or more of the discrete main bodies 38. Portions of the transfer members 212 may also turn between a first position 216 and at least a second position 218 when transferring the main bodies 38 between the first and second moving carrier members 204 and 206. As a result, the main bodies 38 may be turned between a first position 216 and a second position 218. The portions of the transfer members 212 may be turned using rotation assemblies engaged with a portion of each transfer member 212. The main bodies 38 may be turned between certain angles, or about 90 degrees. Optionally, the main bodies 38 may also not be turned at all and the transfer assembly 200 may be used for conveying and/or repitching the main bodies 38 without turning them.

In various embodiments of one or more of picking up, turning, rotating, and repitching the main bodies 38, the transfer surfaces 236 of the transfer members 212 may be configured to retain the main bodies 38 thereto using vacuum. During this overall transferring process, the main body 38 must be securely held by the transfer surface 236 in a manner such that the planned design of the elements of the main body 38 are not dislocated. Of particular interest is to maintain the planned design of the outer cuff 66 which exists along the longitudinal perimeter and having elasticity. By providing the outer cuff 66 configured as described above, the first cuff elastic element 72 having higher tensile force may be securely held to the transfer surface 236 with the aid of the backsheet 60, even though the remaining second cuff elastic element 74 having lower tensile force is not bonded to the backsheet 60. Accordingly, the outer cuff 66 of the present invention secures manufacturing tolerances of the main body 38 during the transfer process illustrated in FIG. 9.

Again referring to FIG. 9, continuous webs 184, 186 for making the front belt 84 and back belt 86 may be moving in parallel towards, over, and away from the second moving carrier member 206 on a roller, conveyor, or other mechanism. In one example, these webs 184, 186 may be continuous, although in other embodiments, they may be discrete components that have been previously cut from a continuous web. An adhesive may be applied to the webs of components or discrete components using adhesive dispensers 228. The adhesive dispensers 228 may apply adhesive to portions of the webs of front and back belts 184, 186 prior to those portions being moved over the second moving carrier member 206. As a result, a main body 38 being transferred to the second moving carrier member 206 may be adhesively attached to the webs of components 220 when transferred onto the second moving carrier member 206. The front waist panel 52 of the main body 38 may be adhesively attached to the continuous web of front belts 184 and the rear waist panel 54 of the main body 38 may be adhesively attached to the continuous web of back belts 186. This may form a web of absorbent articles 10. The web of absorbent articles 10 may then be folded along the transverse centerline T1, seamed, and separated into discrete absorbent articles of the pant type.

Opacity Method

Opacity is measured using a 0° illumination/45° detection, circumferential optical geometry, spectrophotometer with a computer interface such as the HunterLab LabScan XE running Universal Software (available from Hunter Associates Laboratory Inc., Reston, Va.) or equivalent instrument. Instrument calibration and measurements are made using the standard white and black calibration plates provided by the vendor. All testing is performed in a room maintained at 23±2° C. and 50±2% relative humidity.

The spectrophotometer is configured for the XYZ color scale, D65 illuminant, 10° standard observers, with UV filter set to nominal. The instrument is standardized according to the manufacturer's procedures using the 0.7 inch port size and 0.5 inch area view. After calibration, the software is set to the Y opacity procedure which prompts the operator to cover the sample with either the white or black calibration tile during the measurement.

Articles are pre-conditioned at 23° C.±2 C.° and 50%±2% relative humidity for two hours prior to testing. To obtain a specimen, the article is stretched flat on a bench, body facing surface upward, and the total longitudinal length of the article is measured. A testing site on the inner and outer cuffs 64, 66 is selected at the longitudinal midpoint of the article. Using scissors, a test specimen is cut 60 mm long by the entire height of the inner cuff 64 centered at the longitudinal midpoint of the left cuff. Next, a second test specimen is cut, this time from the outer cuff 66, 60 mm long by the entire height of the outer cuff 66, centered at the longitudinal midpoint of the left outer cuff 66. In like fashion, inner and outer cuff 64, 66 specimens are prepared from the cuffs on the right side of the article.

The specimen is placed over the measurement port. The specimen should completely cover the port with the surface corresponding to the inner-facing surface of the cuff directed toward the port. The specimen is gently extended until taut in its longitudinal direction so that the cuff lies flat against the port plate. Adhesive tape is applied to secure the cuff to the port plate in its extended state for testing. Tape should not cover any portion of the measurement port. The specimen is then covered with the white standard plate. A reading is taken, then the white tile is removed and replaced with the black standard tile without moving the specimen. A second reading is taken, and the opacity is calculated as follows:

$$\text{Opacity} = (Y \text{ value}_{(black\ backing)} / Y \text{ value}_{(white\ backing)}) \times 100$$

Specimens from five identical articles (10 inner cuff (5 left and 5 right) and 10 outer cuff (5 left and 5 right)) are analyzed and their opacity results recorded. The average opacity for the inner cuffs 64 and the outer cuffs 66 are calculated and report separately, each to the nearest 0.01%.

Air Permeability Test

Air permeability is tested using a TexTest FX3300 Air Permeability Tester (available from Advanced Testing Instruments, Greer, S.C.) with a custom made 1 cm² circular aperture (also available from Advanced Testing Instruments) or equivalent instrument. The instrument is calibrated according to the manufacturer's procedures. All testing is performed in a room maintained at 23° C.±2 C.° and 50%±2% relative humidity.

The articles are pre-conditioned at 23° C.±2 C.° and 50%±2% relative humidity for two hours prior to testing. To obtain a specimen, the article is stretched flat on a bench, body facing surface upward, and the total longitudinal length of the article is measured. A testing site on the inner and outer cuffs 64, 66 is selected at the longitudinal midpoint of the article. Using scissors, a test specimen is cut 30 mm long by the entire height of the inner cuff 64 centered at the longitudinal midpoint of the left cuff. Next, a second test specimen is cut, this time from the outer cuff, 30 mm long by the entire height of the outer cuff 66, centered at the longitudinal midpoint of the left outer cuff 66. In like fashion, inner and outer cuff 64, 66 specimens are prepared from the cuffs on the right side of the article. Any elastic members are removed.

The specimen is centered over the measurement port. The specimen should completely cover the port with the surface corresponding to the inward-facing surface of the cuff directed toward the port. The specimen is gently extended in its longitudinal direction until taut so that the cuff lies flat across the port. Adhesive tape is applied to secure the cuff across the port in its extended state for testing. Tape should not cover any portion of the measurement port. The test pressure is set to allow air to pass through the specimen. For non-woven cuffs the pressure is set for 125 Pa and for cuffs containing films 2125 Pa is used. The sample ring is closed and the measuring range is adjusted until the range indicator shows green to indicate that the measurement is within the accepted limits of the instrument. The air permeability is recorded to the nearest 0.1 $m^3/m^2/min$.

Hydrostatic Head Test

Hydrostatic head is tested using a TexTest FX3000 Hydrostatic Head Tester (available from Advanced Testing Instruments, Greer, S.C.) with a custom made 1.5 $cm^2$ circular measurement port (also available from Advanced Testing Instruments). Two annular sleeve rings, the same dimensions as the gaskets around the measurement ports, are cut from the standard protective sleeves for fine nonwovens (part FX3000-NWH, available from Advanced Testing Instruments). The sleeve rings are then adhered with two-sided adhesive tape to the sample facing surfaces of the upper and lower gaskets of the TexTest instrument to protect the specimen during clamping. Standardize the instrument according to the manufacturer's procedures. All testing is performed in a room maintained at about 23° C.±2 C.° and about 50%±2% relative humidity.

Precondition the articles at about 23° C.±2 C.° and about 50%±2% relative humidity for two hours prior to testing. To obtain a specimen, lay the article stretched flat on a bench, body facing surface upward, and measure the total longitudinal length of the article. Select a testing site on the inner and outer cuffs 64, 66, at the longitudinal midpoint of the article. Using scissors cut a test specimen 70 mm long by the entire height of the inner cuff 64 centered at the longitudinal midpoint of the left cuff. Next cut a second test specimen, this time from the outer cuff, 70 mm long by the entire height of the outer cuff 66, centered at the longitudinal midpoint of the left outer cuff. In like fashion, prepare inner and outer cuff 64, 66 specimens from the cuffs on the right side of the article. Any elastic members are removed.

Place the specimen centered over the port of the upper test head. The specimen should completely cover the port with the surface corresponding to the outward-facing surface of the cuff directed toward the port (inner-facing surface will then be facing the water). Gently extend the specimen taut in its longitudinal direction so that the cuff lies flat against the upper test plate. Adhesive tape is applied to secure the cuff to the test plate in its extended state for testing. Tape should not cover any portion of the measurement port.

Fill the TexTest syringe with distilled water, adding the water through the measurement port of the lower test plate. The water level should be filled to the top of the lower gasket. Mount the upper test head onto the instrument and lower the test head to make a seal around the specimen. The test speed is set to 3 mbar/min for samples that have a hydrostatic head of 50 mbar or less and a speed of 60 mbar/min for samples with a hydrostatic head above 50 mbar. Start the test and observe the specimen surface to detect water droplets penetrating the surface. The test is terminated when one drop is detected on the surface of the specimen or the pressure exceeds 200 mbar. Record the pressure to the nearest 0.5 mbar or record as >200 mbar if there was no penetration detected.

A total of five identical articles (10 inner cuff and 10 outer cuff specimens) are analyzed and their hydrostatic head results recorded. Calculate and report the average hydrostatic head for the inner cuffs 64 and the outer cuffs 66 and report each to the nearest 0.1 mbar.

EXAMPLES

Example 1

A pant type absorbent article having the cuff configuration of FIG. 2, using a nonwoven material of the SMS type available from Toray Polytech Nantong with tradename LIVSEN SMS 15 as cuff layer 100, and having dimensions as follows.

| | |
|---|---|
| Distance of first cuff elastic element 72 to cuff sealing 76 | 8 mm |
| Distance between the one elastic body of the first cuff elastic element 72 and most inwardly disposed elastic body of the second cuff elastic element 74 | 3 mm |
| Distance between the two elastic bodies of the second cuff elastic element 74 | 3 mm |
| Transverse width of cuff fringe 78 | 7 mm |
| Percentage of tensile force of each elastic body of the second cuff elastic element 74 compared to the one elastic body of the first cuff elastic element 72 | 54% |

Example 2

A pant type absorbent article having the cuff configuration of Example 1 except having the inner cuff formed by only one layer (similar to the inner cuff of FIG. 10) and using a nonwoven material of the SMNS type available from PGI Spain with tradename CoPHOB15 P11 V as cuff layer 100.

Comparative Example 1

Figure 10:
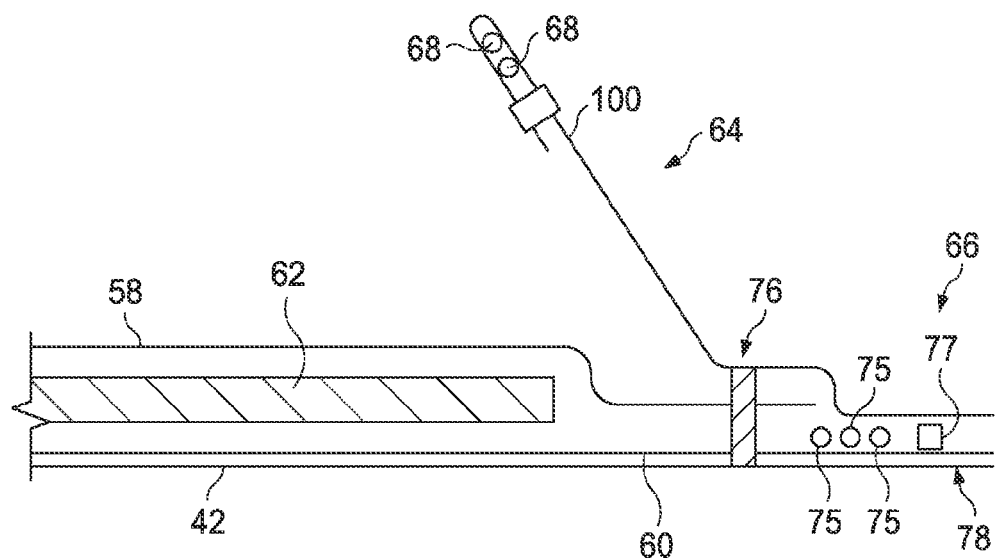
FIG. 10 is a schematic cross section view of an embodiment of the outer cuff of the prior art.

A pant type absorbent article made of the same material and structure as Example 1, except taking the inner and outer cuff 64, 66 configuration of FIG. 10, and having dimensions as follows.

| | |
|---|---|
| Distance of outer cuff elastic element 75 to cuff sealing 76 | 8 mm |
| Distance between each of the three elastic bodies of the outer cuff elastic element 75 | 3 mm + 3 mm |
| Transverse width of cuff fringe 78 | 7 mm |
| Tensile force of each of the three elastic bodies of the outer cuff elastic element 75 | Same(*) |

(*)Each of the elastic bodies had the same tensile force as the first cuff elastic element 72 of Example 1.

Compared to Comparative Example 1, Examples 1 and 2 provide improvement in one or more of: tactile and perceived softness, softness of leg cuff, and fit to legs, while maintaining the performance of leakage protection.

Consumer Acceptance

Example 1 and Comparative Example 1 including an identical absorbent core were subjected to a consumer test for application on 50 panelists and 51 panelists, respectively. The panelists were caregivers of Japanese Size 4 (L-size) wearers of age 0-36 months, and at about the same boy/girl ratio. The caregivers of the panelists were given enough products to use either product for 5 days, and then answer a questionnaire including the following questions, and asked to rate the performance in 5 scales from "Very Poor" to "Excellent", wherein 100 represents "Excellent", 75 represents "Good", 50 represent "Fair", 25 represent "Poor" and 0 represents "Very Poor". The ratings were averaged and statistically analyzed. Test results are shown below in Table 3.

TABLE 3

| Question | Example 1 | Comparative Example 1 |
|---|---|---|
| Overall Rating | 77* | 69 |
| Overall Fit Of The Pant When The Diaper Is Full | 72 | 64 |
| Softness of leg cuff | 80* | 69 |

*Statistically significant over Comparative Example 1 with 90% confidence level

According to the consumer acceptance test results, Example 1 of the present invention, compared to Comparative Example 1, was accepted better in all aspects of the product listed above, and was statistically significantly better accepted in "Overall Rating" and "Softness of leg cuff".

The dimensions and values disclosed herein are not to be understood as being strictly limited to the exact numeral values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a skin facing side, a garment facing side, a longitudinal axis, and a transverse axis, the absorbent article comprising:
   1) a water permeable topsheet extending in the longitudinal direction and the transverse direction;
   2) a water impermeable backsheet extending in the longitudinal direction and the transverse direction, and having a pair of longitudinal side edges;
   3) an absorbent core disposed between the topsheet and the backsheet, the backsheet extending beyond the absorbent core in both the longitudinal direction and the transverse direction;
   4) an outer cover layer disposed on the garment facing side of the backsheet, the outer cover layer at least coextensive with the backsheet; and
   5) a pair of outer cuffs for providing leg gasketing function, each outer cuff comprising:
      a) a cuff sealing disposed in a longitudinally extending manner, the cuff sealing located transversely between the absorbent core and the longitudinal side edge of the backsheet,
      b) a first cuff elastic element comprising at least one elastic body disposed in a longitudinally extending manner, the first cuff elastic element located transversely inward of the longitudinal side edge of the backsheet, and no more transversely inward than 3 mm from the cuff sealing;
      c) a second cuff elastic element comprising at least one elastic body disposed in a longitudinally extending manner, the second cuff elastic element located transversely outward of the longitudinal side edge of the backsheet; wherein the tensile force of each elastic body of the second cuff elastic element is no more than 70% of the tensile force of any elastic body of the first cuff elastic element;
      d) a cuff gap located between the of the first cuff elastic element and the second cuff elastic element, the cuff gap having a transverse width of at least 3 mm; and
      e) a cuff fringe disposed in a longitudinally extending manner, the cuff fringe located transversely outward the second cuff elastic element, the cuff fringe having a transverse width of at least 5 mm;
      wherein the cuff sealing bonds all of the materials existing in the thickness direction of the article where the cuff sealing is located.

2. The article of claim 1 wherein the first cuff elastic element comprises at least one elastic body, the first cuff elastic element having a density of accumulatively no more than 1500 dtex.

3. The article of claim 2 wherein any elastic body of the first cuff elastic element is prestretched no more than 330%.

4. The article of claim 2 wherein the first cuff elastic element is one elastic body.

5. The article of claim 2 wherein the first cuff elastic element is located transversely outward the cuff sealing.

6. The article of claim 2 wherein the second cuff elastic element comprises at least one elastic body, any elastic body of the second cuff elastic element having no more than 680 dtex.

7. The article of claim 6 wherein any elastic body of the second cuff elastic element is prestretched no more than 300%.

8. The article of claim 6 wherein the second cuff elastic element is made of more than one elastic body.

9. The article of claim 8 further comprising a cuff layer for at least partially supporting the second cuff elastic element.

10. The article of claim 9 wherein the first cuff elastic element is located between the topsheet and the backsheet, and the second cuff elastic element is located between the cuff layer and the outer cover layer.

11. The article of claim 9 wherein the first cuff elastic element and the second cuff elastic element are located between two layers of the cuff layer.

12. The article of claim 9 further comprising an inner cuff formed by the cuff layer, the inner cuff extending transversely inward from the cuff sealing.

13. The article of claim 1 wherein the first cuff elastic element and the second cuff elastic element are located between two layers of the outer cover layer.

14. The article of claim 13 further comprising an inner cuff formed by a cuff layer, the inner cuff extending transversely inward from the cuff sealing.

15. The article of claim 14, wherein the cuff layer comprises an N-fiber material.

16. The article of claim 12, wherein the inner cuff has a hydrostatic head of greater than about 2 mbar and the outer cuff has a hydrostatic head of less than about 200 mbar.

17. The article of claim 12, wherein the inner cuff has an opacity of from about 15% to about 50% hunter opacity and the outer cuff has an opacity of from about 45% to about 75% hunter opacity.

18. The article of claim 12, wherein the inner cuff has an air permeability of less than about 50 $m^3/m^2$/min and the outer cuff has an air permeability of greater than about 5 $m^3/m^2$/min.

19. The article of claim 2 wherein the article is a taped diaper.

20. The article of claim 1, wherein the article is a pant-type diaper comprising a main body and a ring-like elastic belt comprising a front belt, a back belt; and wherein the main body comprises the topsheet, the backsheet, the absorbent core, the nonwoven outer cover layer, and the outer cuff.

21. The article of claim 20 wherein the center of the front belt is joined to a front waist panel of the main body, the center of the back belt is joined to a back waist panel of the main body, the front and back belt each having a left side panel and a right side panel where the main body does not overlap, and the transverse edges of the front belt and the back belt are joined by a seam to form a waist opening and two leg openings, each front belt and back belt having transversely continuous proximal and distal edges, the proximal edge being located closer than the distal edge relative to the longitudinal center of the article; wherein each of the front belt and back belt are formed by an inner sheet, an outer sheet, and a plurality of elastic bodies sandwiched therebetween and running in the transverse direction.

22. The article of claim 21 wherein the front belt, back belt, and the main body are configured such that the tensile force of any of the first and second cuff elastic elements are not transmittable to any elastic body of the elastic belt.

23. The article of claim 22 wherein any elastic body of the elastic belt is located longitudinally outward of the first and second cuff elastic elements.

24. The article of claim 22 wherein the main body and elastic belt are not joined with each other at locations where the elastic body of the elastic belt and the first and second cuff elastic elements overlap in the thickness direction of the article.

25. A process for manufacturing the article claim 20, comprising the steps of:
    a) advancing a continuous web of the front belt and a continuous web of the back belt in parallel;
    b) advancing a continuous web of the main body;
    c) separating the continuous web of the main body into discrete main bodies;
    d) picking up the discrete main body by a transfer surface wherein the main body is held on the transfer surface by vacuum; and
    e) transferring the main body on to the continuous webs of the front and back belts.

26. The process of claim 25 further comprising the step of turning the discrete main body substantially 90 degrees between the pickup step and the transfer step.

* * * * *